United States Patent [19]

Mahoney et al.

[11] Patent Number: 5,976,439
[45] Date of Patent: Nov. 2, 1999

[54] ALGINATE ROPES, METHOD OF PREPARATION AND USE

[75] Inventors: Peter M. J. Mahoney, Powys; Bryan Griffiths, Gwent; John Charles Fenton, Rhymney, all of United Kingdom

[73] Assignee: Bristol-Myers Squibb Company, New York, N.Y.

[21] Appl. No.: 08/817,752

[22] PCT Filed: Oct. 27, 1995

[86] PCT No.: PCT/EP95/04253

§ 371 Date: Jun. 27, 1997

§ 102(e) Date: Jun. 27, 1997

[87] PCT Pub. No.: WO96/14453

PCT Pub. Date: May 17, 1996

[30] Foreign Application Priority Data

Nov. 2, 1994 [GB] United Kingdom .................... 9422343

[51] Int. Cl.$^6$ ....................................... D01D 5/14
[52] U.S. Cl. ........................ 264/181; 264/176.1; 264/180; 264/173.12; 264/339
[58] Field of Search ...................... 264/164, 266, 264/288.4, 291, 531, 339, 181, 176.1, 180, 173.12

[56] References Cited

PUBLICATIONS

Water–Soluble Alginate Salt Fibers and Their Manuf. Using Red. Amts of Org Solv.
Pulp–Based Foam Ropes or Beads and their Manuf.

*Primary Examiner*—Merrick Dixon
*Attorney, Agent, or Firm*—John M. Kilcoyne; Theodore R. Furman, Jr.

[57] ABSTRACT

A process for preparing an alginate rope, which process comprises the steps of: (a) extruding an aqueous solution of a water soluble alginate into a coagulation bath; (b) contacting the extruded water soluble alginate with a source of a cation capable of forming a water insoluble alginate salt so as to produce a tow of water insoluble alginate fibers; (c) twisting the water insoluble alginate fibers of the tow; and (d) stretching the fibers up to 250% of their original length. The alginate rope prepared according to the process of the invention may be used as a surgical pack material or in the treatment of cavity wounds.

13 Claims, No Drawings

ALGINATE ROPES, METHOD OF PREPARATION AND USE

The present invention relates to a process for the preparation of an alginate rope, an alginate rope prepared according to that process, a dressing comprising the alginate rope and methods of use thereof.

Alginate fibres have been known for some time as being useful in the preparation of surgical dressings. For example, United Kingdom Patent No. 653341, published in 1951, describes surgical dressings formed from fibres of calcium alginate. The employ of alginate fibres is often desirable over other conventional materials employed in surgical dressings, such as cotton and the like, in view of the superior biocompatibility properties of alginates.

Calcium alginate fibres have subsequently been modified to improve their relative insolubility in water or wound exudate matter. Bonniksen in GB-A-653341 therefore proposed that a proportion of the insolubilising calcium ions in calcium alginate be replaced by solubilising sodium cations. The resulting process has become known as "conversion" of calcium alginate to form a mixed salt alginate. Such mixed salt alginates exhibit a further advantage associated in the employ of alginates in wound treatment, in that such mixed salt alginates having improved solubility in water or wound exudate matter form a protective and useful gel like structure that results over time, and is beneficial to the wound healing process.

Skilled artisans are therefore well aware that it is often desirable to employ alginates in wound dressings and various types of dressing formed from fabrics comprising alginate fibres are therefore known, including non-woven alginate rope. Alginate rope is particularly useful for surgical packing and the management of cavity wounds.

Alginate rope is conventionally prepared via a multistage process involving extruding an aqueous solution of sodium alginate into a calcium ion source, stretching the resulting calcium alginate fibres to between 160 and 250% of their original length, optionally converting a proportion of the calcium ions to sodium ions, then crimping, cutting to staple length, carding and textilling the tow.

Such multistage processes are time consuming and expensive, inter alia, involving the use of multiple spinnerets. Furthermore, alginate ropes produced by conventional techniques as described above generally lack structural integrity which often results in unravelling thereof during use or disintegration on removal from a wound site, whereby residual alginate fibre can be left in the wound site. The residual fibres are generally picked out in tiny pieces, or removed by irrigation, from the wound site. Such removal requires considerable skill, and there is therefore a need for an alginate rope which can be lifted from a wound in one piece. An example of a currently employed alginate rope is available under the trade mark SORBSAN, this SORBSAN rope being a thin sliver which often lacks structural strength and use thereof can therefore be disadvantageous for the reasons described above.

In view of the above lack of structural integrity associated with commercially available alginate rope products, other materials, such as cotton gauze and the like, are often employed in situations where it might have been desirable to employ alginate rope products, such as in the treatment of sinus cavities and the like. Such alternative materials, cotton gauze being a typical example, lack the abovedescribed advantageous biocompatibility or gel-forming properties associated with alginates.

We have now discovered a process of preparation, and a resulting alginate rope product, which alleviate the above problems. In particular, we have discovered a process of preparing an alginate rope which is essentially a single stage process and eliminates the necessity to employ the above described steps of crimping, cutting, carding and textilling the tow. Furthermore, an alginate rope product is provided by the present invention which exhibits greatly improved structural integrity, this being advantageous, inter alia, in handling the dressing before application to a wound site and in many cases makes removal from a deep wound site much easier.

There is therefore provided by the present invention a process of preparing alginate rope, which process comprises the steps of:

(a) extruding an aqueous solution of a water soluble alginate into a coagulation bath;
(b) contacting the extruded water soluble alginate with a source of a cation capable of forming a water insoluble alginate salt so as to produce a tow of water insoluble alginate fibres;
(c) twisting the water insoluble alginate fibres of the tow; and
(d) stretching the fibres up to 250% of their original length.

Water soluble alginates include, for example, sodium alginate, potassium alginate, lithium alginate, ammonium alginate and magnesium alginate. Preferably the water soluble alginate used in the process of the present invention is sodium alginate. Suitably the aqueous solution of the water soluble alginate is extruded into a coagulation bath containing a source of a cation capable of forming a water insoluble alginate salt.

Cations capable of forming water insoluble alginate salts include, for example, calcium and zinc cations. Preferably the cation capable of forming a water insoluble alginate used in the process of the present invention is calcium ion.

Suitably the source of the insolubilising cation comprises a salt thereof, such as chlorides, sulphates, nitrates, gluconates and the like. Aptly a chloride salt of the insolubilising cation is employed.

It may be preferred to prepare a mixed salt alginate rope product whereby at least some of the insolubilising cations of the alginate fibres produced by step (b) are replaced by cations capable of forming a water soluble alginate salt. Optionally, a process according to the present invention comprises, following step (d), treating the water insoluble alginate fibres with a source of a cation capable of forming a water soluble alginate salt so as to replace at least some of the insolubilising cations present in the alginate fibres with cations capable of forming a water soluble alginate salt.

Suitably, preparation of a mixed salt alginate may be achieved by treating sequentially with an acid and a source of a cation capable of forming a water soluble alginate. Generally an acid bath is used in the conversion procedure for treatment with a suitable acid and a solubilising cation. Desirably the pH should be carefully controlled during the conversion procedure in order to avoid removal of more than the desired percentage of calcium cations, suitably at least 10% of the insolubilising cations are removed. In a particularly preferred embodiment no more than about 20% of the insolubilising cations are removed. Typically, during acid treatment, the pH of the bath should be in the range of 1 to 3, aptly about 1.5 to 2.5. Control of pH can be achieved by standard techniques, such as titration of the acid bath and the like.

Suitably organic or inorganic acids can be used in the treatment of the water insoluble alginate fibres. Aptly mineral acids such as hydrochloric, sulphuric and nitric acids may be employed, hydrochloric generally being preferred.

The retention time, which is to say the time for which the insoluble alginate is in contact with the acidic medium, may be any suitable period of time, for example from 1 second to 5 minutes. Retention times in the order of from 5 to 60 seconds such as about 20 or 30 seconds are quite suitable. It will be appreciated that the degree of conversion may be controlled by a combination of the pH of the acid bath and the retention time.

Suitable basic sources of a cation capable of forming a water soluble alginate include, for example, salts such as carbonates, hydroxides and the like, of solubilising cations such as sodium, potassium, lithium, ammonium and magnesium as hereinbefore described.

In a preferred embodiment, the present invention provides a process for the preparation of an alginate rope comprising 30:70 Ca:Na to 90:10 Ca:Na mixed salt alginate fibres, suitably 40:60 Ca:Na to 90:10 Ca:Na, more suitably 60:40 Ca:Na to 85:15 Ca:Na and even more suitably 70:30 Ca:Na to 85:15 Ca:Na. In a particularly preferred embodiment the present invention provides a process for the preparation of alginate rope comprising about 80:20 Ca:Na mixed salt alginate fibres.

Aptly the fibres are extruded at a linear speed in the range of 1 meter/minute to 40 meters/minute, more aptly at a speed in the range of 3 meters/minute to 20 meters/minute, even more aptly at a speed in the range of 4 meters/minute to 10 meters/minute, and preferably at about 5 meters/minute.

Suitably, twisting of the water insoluble alginate fibres is achieved by extruding the fibres from a spinneret which is rotated at a speed in the range of 3 to 800 rpm, more suitably at a speed of 3 to 400 rpm, most suitably at a speed of 3 to 100 rpm, and preferably 3 to 50 rpm.

The number of holes and hole size of the spinneret employed in the present invention varies depending on the nature of the required end product. Generally, spinnerets having a hole size of 20 to 200 microns in diameter are employed, suitably 40 to 120 microns and more suitably 60 to 80 microns. Aptly a spinneret having 100 to 400 holes may be employed in the preparation of thin sliver alginate rope product, typically of thickness 0.8 to 1.2 mm, which can be subsequently employed in the production of a yarn suitable to be textilled to provide surgical swabs, dressing fabrics and the like. Alternatively, a 5,000 to 10,000 hole spinneret can be used to prepare a relatively thicker alginate rope product, suitably of 2 to 4 mm, for example of 2.8 to 3.2 mm in thickness, which is itself suitable for use in sinus cavities and the like without further significant processing. (It will be appreciated that although these are termed ropes, they often appear ribbon-like).

In addition to the above variation in the number of holes and hole size, it may be desirable to vary the hole pattern provided on the spinneret. For example, the holes may be substantially evenly distributed over the spinneret face, alternatively a denser population of holes may be provided in a localised region of the spinneret face. The spinneret may be of variable cross sectional shape, such as circular, rectangular and the like.

It is generally preferred that step (d) comprises stretching the water insoluble alginate fibres in the range of 120 to 200%, suitably 140 to 180% of their original length, and more suitably the fibres are stretched to 150 to 170% of their original length.

Suitably a process according to the present invention further comprises washing the alginate rope, generally with deionised water, and aptly may also include a drying step. Suitably the drying involves treatment of the rope with a volatile drying agent and/or drying in air suitably by employing a stream of hot air. Apt drying agents include methyl alcohol, ethyl alcohol, isopropyl alcohol, acetone and the like, suitably acetone being generally employed in the present process.

As hereinbefore described an alginate rope product according to the present invention is advantageous in terms of its structural integrity and there is provided by the present invention an alginate rope having a dry tensile strength of at least 75 N/g. There is further provided by the present invention an alginate rope having a wet tensile strength of at least 25 N/g.

The terms 'dry tensile strength' and 'wet tensile strength' as used herein denote the maximum load to breaking per gram of sample, the former relating to a dry sample and the latter relating to a wet sample suitably saturated by an appropriate solvent, such as ringers solution and the like. Further details of the 'dry tensile strength' and the 'wet tensile strength' are given in the accompanying Examples. All numbers in N/g herein obtained using a 10 cm gap between jaws on test rig.

Aptly an alginate rope according to the present invention has a dry tensile strength of at least 150 N/g and more aptly at least 200 N/g. In terms of wet tensile strength an alginate rope according to the present invention suitably has a strength of at least 50 N/g, and more suitably at least 100 N/g.

An alginate rope according to the present invention suitably has an absorbency in the range of 1 to 10 g of ringers solution per g of alginate rope, and more suitably an absorbency in the range of 2 to 6 g of ringers solution per g of alginate rope.

Alginates are produced by a variety of micro-organisms and marine algae which are the normal commercial source. The alginates being natural materials show considerable variety but are characterised in being block copolymers, the individual monosaccharide units being arranged into groups as blocks of mannuronic (M) and guluronic (G) residues. In addition to the repeating blocks each polymer chain can contain a proportion of alternating M and G monosaccharide units.

Suitably alginate fibres-employed in the absorbent layer may be high M or high G, typically 60–80% by weight M or G respectively.

It is generally preferred however that when it is required to obtain an alginate rope of relatively high tensile strength, such as 250 N/g to 350 N/g dry tensile strength or 140 N/g to 150 N/g wet tensile strength, a high G alginate is employed. Such a high G alginate rope according to the present invention is typically capable of absorbing 2 to 4 g of ringers solution per g of alginate rope. Alternatively if it is required to obtain a relatively more absorbent alginate rope according to the present invention, suitably having an absorbency of 4 to 6 g of ringers solution per g of alginate rope, such a rope having relatively lower dry tensile strengths and wet tensile strengths of 200 N/g to 250 N/g and 125 N/g to 135 N/g respectively, it is generally preferred to employ a high M alginate.

An advantage associated with a process according to the present invention is that by varying the relative rotational speed of the spinneret, and linear extrusion speed achieved thereby, the strength and absorptive properties of the resultant rope can be varied. For example, in the case where a relatively strong rope product is required, suitably as described above with a dry tensile strength in the range of 250 N/g to 350 N/g or a wet tensile strength in the range of 140 N/g to 150 N/g and capable of absorbing 2 to 4 g of ringers solution per g of alginate, the fibres are extruded at a speed in the range of 4 to 10 meters/minute (preferably 5 meters/minutes) and the spinneret is rotated at a speed in the range of 33 to 37 rpm (preferably 35 rpm). In an alternative embodiment, wherein it is required to obtain a more absorptive rope as described above, typically being capable of absorbing 4 to 6 of ringers solution per g of alginate, and having a dry tensile strength of 200 N/g to 250 N/g or a wet tensile strength of 125 N/g to 135 N/g, the relative linear and rotational speeds are suitably 4 to 10 meters/minute (preferably 5 meters/minute) and 28 to 32 rpm (preferably 30 rpm).

Typically an alginate rope having a dry tensile strength in the range of 250 N/g to 350 N/g or a wet tensile strength in the range of 140 N/g to 150 N/g prepared as above is particularly suitable for use as in the preparation of yarns and woven fabrics, wherein structural integrity is desirable in order to withstand the stresses imparted by conventional knitting procedures. Furthermore, alginate rope products exhibiting the above-mentioned strength are suitable for use as gingival retraction cords, wherein a highly twisted product may be desirable for facilitating arrangement of the cord around the bed of a tooth; skilled workers can appreciate that a loosely twisted product can be disadvantageous in that an insertion implement, such as a spatula or the like, could pass through gaps in the loosely twisted product thereby making arrangement of the cord around the bed of the tooth problematic. On the other hand, the provision of a more absorptive rope as described above is particularly suitable for use in the treatment of highly exuding wounds, sinus cavities and the like. In conjunction with the above-mentioned absorptive properties, such ropes would exhibit a tensile strength of a dry tensile strength of 200 N/g to 250 N/g or a wet tensile strength of 125 N/g to 135 N/g, thereby facilitating removal thereof from a wound site or cavity.

There is further provided by the present invention an alginate rope obtained by a process substantially as hereinbefore described.

An alginate rope according to the present invention is suitably of 1 to 4 mm in thickness, 6 to 10 mm wide and is cut to a required length depending on the desired application.

Both high M and high G ropes according to this invention offer the advantages of excellent dimentional stability which make application of a dressing consisting of or comprising the role particularly easy to deep or cavity wounds such as sinuses. In use high G containing dressings are particularly good in retaining their integrity even after extended periods present in the deep or cavity wounds so that removal of the intact or largely intact dressing is greatly facilitated. This is a particular advantage of such dressings of the invention since removal of traditional dressings from deep or cavity wounds is a considerable problem often requiring significant nursing time. In use high M containing dressings can dissolve in wound exudate allowing for the dressings to be removed by washing out the wound with sterile saline solution, water or the like.

The dressing of this invention may simply consist of the alginate rope presented in suitable lengths, for example from 1 to 30 cms, more usually 2 to 20 cms, for example 10 or 15 cm lengths. The dressing most aptly is provided sealed in a bacteria proof pouch or pack, for example of foil, plastics or even an appropriate paper. Such pouches and packages are well known to the skilled worker as are methods of sealing and sterilizing.

From one aspect this invention provides a ribbon-like dressing suitable for dressing cavity wounds, which dressing comprises twisted alginate fibres whereby enhanced dimensional stability is produced. By enhanced dimensional stability it is meant that at least 4 times, more aptly at least 8 times and preferably at least about 10 times as much force is required to pull the dressing apart (perpendicular to its length) than in an analogous dressing wherein the alginate fibres are untwisted.

The present invention will now be further illustrated by the following examples which do not limit the scope of the invention in any way.

EXAMPLE 1

A 4 to 60% by weight sodium alginate solution in water was extruded into a 12 liter spin bath containing a 0.2M aqueous solution of calcium chloride at 25° C. The alginate solution was extruded at a linear rate of 1.5 meter/minute through a spinneret (10000 holes, 75 microns) rotating at 10 rpm. The tow was drawn from the spinneret to give a linear draw ratio of 1.2. The fibres were stretched to 160 to 170% of their original length.

The product was then collected, washed in water, dried in acetone (20 mls acetone per gram alginate; with a specific gravity of acetone in the range of 0.82–0.83) and air dried in an air stream at 25° C.

EXAMPLE 2

The tensile properties of a rope obtained by Example 1 and those of a known alginate rope commercially available under the trade mark SORBSAN were investigated.

In order to determine the tensile strengths of an alginate rope according to the present invention the following test conditions were employed:

Test Speed: 100.0 mm min$^{-1}$

Gauge Length: 100.0 mm

Load Cell: 500.0 N

Cell Class: 0.5%

Test conditions employed in the analysis of SORBSAN (trade mark) were as follows:

Test Speed: 20.0 mm min$^{-1}$

Gauge Length: 100.0 mm

Load Cell: 20.0 N

Cell Class: 0.5%

The test speed and load cells employed in the analysis of SORBSAN (trade mark) were lower than those for the alginate rope according to the present invention due to the lack of integrity observed for SORBSAN (trade mark). Similarly, both dry and wet tensile strengths were investigated for the rope of the present invention whereas only the dry tensile strength was investigated for SORBSAN (trade mark) due to the weakness of the product.

In order to investigate the wet tensile strength of the rope according to the present invention, the rope was soaked in ringers solution (142 millimoles of sodium ions and 2.5 millimoles of calcium ions) for 1 hour. After this time, the ringers solution was poured away and any excess liquid was allowed to drain prior to performing the test.

Tensile test results for the dry materials:

|  | Max Load | Work Done (N-mm) |
|---|---|---|
| High G alginate rope according to the present invention (2.07 g/m) | 63.57 (±12.60) | 1557.0 (±737.0) |

-continued

|  | Max Load | Work Done (N-mm) |
| --- | --- | --- |
| High M alginate rope according to the present invention (2.07 g/m) | 48.32 (±11.43) | 1332.0 (±642.0) |
| SORBSAN (trade mark) (2.18 g/m) | 0.22 (±0.14) | 2.3 (±1.9) |

Tensile test results for samples according to the invention soaked in ringers solution for 1 hour were as follows:

|  | Max Load | Work Done (N-mm) |
| --- | --- | --- |
| High G alginate rope according to the present invention (2.07 g/m) | 29.84 (±4.03) | 1212 (±186.0) |
| High M alginate rope according to the present invention (2.07 g/m) | 26.23 (±3.72) | 1183 (±143.0) |

EXAMPLE 3

The absorbencies of a 60% M alginate rope and a 60% G alginate rope according to the present invention were investigated.

The results are shown in Tables 1 and 2.

EXAMPLE 4

A 4 to 6% by weight sodium alginate solution in water at 20° C. was extended into a 121 spin bath containing 0.2 m aqueous calcium chloride solution at 20° C. The alginate was a high G alginate. The fibres were extruded at a speed of 5 meter/minute through a spinneret (10,000 holes, 75 microns) rotated at 35 rpm. The resulting two was treated as described in Example 1 to provide a particularly strong rope.

EXAMPLE 5

Using the method of Example 3 but employing a high M alginate and a rotational speed of 35 rpm, a particularly absorptive rope was obtained.

EXAMPLE 6

In order to compare the integrity and elasticity of the dressing of Example 3 and an analogous rope produced without rotation, the materials were tested perpendicular to the axis of spinning and testing involved, not breaking the sample, but extending the sample and returning the sample to the starting position.

All tensile tests were performed using the LLoyd LR5K material testing apparatus. The method involved using a set of clamps to hold the dressings (ropes) in place. Tests were performed by clamping approximately 5 mm of the fibre perpendicular to the axis of spinning. A seven fold extension was then applied to the fibre and following the extension the fibre was allowed to return to the starting position. This Sample: 60% M alginate rope (RINGERS SOLUTION - 30 MINUTES)

| Sample No. | Weight of intact dressing (g) $W_1$ | Length of intact dressing (cm) $L_1$ | Length/unit weight (cm/g) $L_2$ | Weight of sample (g) $W_2$ | Weight after 30 mins (g) $W_3$ | Weight of fluid absorbed (g) $W_3 - W_2$ | Weight g of fluid absorbed/g of dressing (g/g) $(W_3 - W_2)/W_2$ | Weight of fluid absorbed by intact dressing (g) $(W_1(W_3 - W_2))/W_2$ |
| --- | --- | --- | --- | --- | --- | --- | --- | --- |
| 1 | 0.2149 | 9.5 | 44.2 | 0.2149 | 1.3772 | 1.1623 | 5.409 | 5.409 |
| 2 | 0.2093 | 9.5 | 45.4 | 0.2093 | 1.4152 | 1.2059 | 5.762 | 5.762 |
| 3 | 0.2194 | 9.5 | 43.3 | 0.2194 | 1.3501 | 1.1307 | 5.154 | 5.154 |
| 4 | 0.2134 | 9.5 | 44.5 | 0.2134 | 1.1850 | 0.9716 | 4.553 | 4.553 |
| 5 | 0.2053 | 9.5 | 46.3 | 0.2053 | 1.1445 | 0.9392 | 4.575 | 4.575 |
| Mean | 0.2125 | 9.5 | 44.7 | 0.2125 | 1.2944 | 1.0819 | 5.091 | 5.091 |
| S.D. | 0.0054 | 0.0 | 1.2 | 0.0054 | 0.1214 | 0.1191 | 0.527 | 0.527 |

TABLE 2

Sample: 60% G alginate rope (RINGERS SOLUTION - 30 MINUTES)

| Sample No. | Weight of intact dressing (g) $W_1$ | Length of intact dressing (cm) $L_1$ | Length/unit weight (cm/g) $L_2$ | Weight of sample (g) $W_2$ | Weight after 30 mins (g) $W_3$ | Weight of fluid absorbed (g) $W_3 - W_2$ | Weight g of fluid absorbed/g of dressing (g/g) $(W_3 - W_2)/W_2$ | Weight of fluid absorbed by intact dressing (g) $(W_1(W_3 - W_2))/W_2$ |
| --- | --- | --- | --- | --- | --- | --- | --- | --- |
| 1 | 0.2175 | 8.5 | 39.08 | 0.2175 | 0.8412 | 0.6237 | 2.868 | 0.6237 |
| 2 | 0.2253 | 8.5 | 37.73 | 0.2253 | 0.9724 | 0.7471 | 3.316 | 0.7471 |
| 3 | 0.2142 | 8.5 | 39.68 | 0.2142 | 0.9731 | 0.7589 | 3.543 | 0.7589 |
| 4 | 0.2129 | 8.5 | 39.92 | 0.2129 | 0.8180 | 0.6051 | 2.842 | 0.6051 |
| 5 | 0.2081 | 8.5 | 40.85 | 0.2081 | 0.9942 | 0.7861 | 3.778 | 0.7861 |
| Mean | 0.2156 | 8.5 | 39.45 | 0.5156 | 0.9198 | 0.7042 | 3.269 | 0.7042 |
| S.D. | 0.0064 | 0.0 | 1.15 | 0.0064 | 0.0832 | 0.0834 | 0.412 | 0.0834 | cycle was repeated five times. The results of these tests (mean and standard deviation values) were as shown below.

Materials tested i) G fibre of Example 3, 10,000 hole sample ii) Analogous unrotated high G fibre, 10,000 hole sample The test method for the ropes:

Test Speed: 20.0 mm min$^{-1}$

Gauge Length: 3.0 mm

Load Cell: 20.0 N

Cell Class: 0.5%

Tensile test results for the unrotated material:

|          |      | MAX LOAD (N) |      | WORK DONE (N-mm) |
|----------|------|--------------|------|------------------|
| Sample 1 | —    |              | —    |                  |
|          | X    | 0.0238       | X    | 0.1647           |
|          | S.D. | 0.0008       | S.D. | 0.0129           |
| Sample 2 | —    |              | —    |                  |
|          | X    | 0.0228       | X    | 0.1430           |
|          | S.D. | 0.0011       | S.D. | 0.0096           |

Tensile test results for the rotated material of the invention:

|          |      | MAX LOAD (N) |      | WORK DONE (N-mm) |
|----------|------|--------------|------|------------------|
| Sample 1 | —    |              | —    |                  |
|          | X    | 0.0249       | X    | 1.703            |
|          | S.D. | 0.0095       | S.D. | 0.158            |
| Sample 2 | —    |              | —    |                  |
|          | X    | 0.2286       | X    | 1.727            |
|          | S.D. | 0.0094       | S.D. | 0.179            |

The results show good reproducibility, both in terms of the max load and work done for each sample. The most striking feature of the results, however, is the ten-fold increase in max load and work done for the rope of this invention. This demonstrates that the method of the invention adds great integrity of the sample.

We claim:

1. A process for preparing an alginate rope, which process comprises the steps of:

(a) extruding an aqueous solution of a water soluble alginate into a coagulation bath;

(b) contacting the extruded water soluble alginate with a source of a cation capable of forming a water insoluble alginate salt so as to produce a tow of water insoluble alginate fibers;

(c) twisting the water insoluble alginate fibers of the tow; and (d) stretching the fibers up to 250% of their original length.

2. A process as claimed in claim 1 wherein the water soluble alginate is selected from the group consisting of sodium alginate, potassium alginate, lithium alginate, ammonium alginate and magnesium alginate.

3. A process as claimed in claim 1 wherein the cation capable of forming a water insoluble alginate is selected from the group consisting of calcium and zinc.

4. A process as claimed in claim 1 wherein the cation capable of forming a water insoluble alginate is in the form of a salt selected from the group consisting of chlorides, sulphates, nitrates, gluconnates and the like.

5. A process as claimed in claim 1 wherein the process comprises an additional step of treating the water insoluble alginate fibers with a source of a cation capable of forming a water soluble alginate salt so as to replace at least some of the insolubilizing cations present in the alginate fibers with cations capable of forming a water soluble alginate salt.

6. A process as claimed in claim 5 wherein the additional step is preceded by treatment of the fiber with an acid.

7. A process as claimed in claim 5 wherein no more than about 20% of the insolubilizing cations are removed by the additional steps.

8. A process for the preparation of an alginate rope as claimed in claim 15 wherein the rope comprises 30:70 Ca:Na to 90:10 Ca:Na mixed salt alginate fibers, and wherein the process comprises the additional steps of:

(e) contacting the alginate fibers with an acid; and (f) treating the fibers with a source of a cation capable of forming a water soluble alginate salt so as to replace at least some of the insolubilizing cations present in the alginate fibers with cations capable of forming a water soluble alginate salt.

9. A process as claimed in claim 8 wherein steps (e) and (f) are conducted in an acid bath whose contents include a suitable acid and a solubilizing cation.

10. A process as claimed in claim 9 wherein the pH of the acid bath is in the range of 1 to 3.

11. A process as claimed in claim 10 wherein the pH of the acid bath is in the range of about 1.5 to about 2.5.

12. An alginate rope obtained by the process as claimed in claim 1.

13. A method of treating cavity wounds comprising dressing the wound with an alginate rope obtained by the process as claimed in claim 1.

* * * * *